(12) United States Patent
Kiehne

(10) Patent No.: US 7,975,722 B2
(45) Date of Patent: Jul. 12, 2011

(54) ONE WAY VALVE THAT USES FLUID PRESSURE TO OPEN AND CLOSE THE VALVE

(75) Inventor: Bruce Leigh Kiehne, Springwood (AU)

(73) Assignee: Just Innovative Layouts Pty Ltd, Slacks Creek, QLD (AU)

( * ) Notice: Subject to any disclaimer, the term of this patent is extended or adjusted under 35 U.S.C. 154(b) by 986 days.

(21) Appl. No.: 11/578,674

(22) PCT Filed: Apr. 29, 2005

(86) PCT No.: PCT/AU2005/000625
§ 371 (c)(1),
(2), (4) Date: Oct. 17, 2006

(87) PCT Pub. No.: WO2005/107847
PCT Pub. Date: Nov. 17, 2005

(65) Prior Publication Data
US 2007/0251591 A1 Nov. 1, 2007

(30) Foreign Application Priority Data

May 11, 2004 (AU) ................................. 2004902464
Apr. 18, 2005 (AU) ................................. 2005901926

(51) Int. Cl.
*F16K 15/14* (2006.01)
(52) U.S. Cl. .................... 137/854; 251/149.1; 251/149.6
(58) Field of Classification Search .................. 137/844, 137/854; 251/149.1, 149.6
See application file for complete search history.

(56) References Cited

U.S. PATENT DOCUMENTS

| | | | | | |
|---|---|---|---|---|---|
| 4,712,583 | A | * | 12/1987 | Pelmulder et al. | 137/852 |
| 5,190,067 | A | * | 3/1993 | Paradis et al. | 137/1 |
| 5,431,185 | A | * | 7/1995 | Shannon et al. | 137/512.4 |
| 5,578,059 | A | * | 11/1996 | Patzer | 604/249 |
| 5,618,268 | A | * | 4/1997 | Raines et al. | 604/82 |
| 5,771,935 | A | | 6/1998 | Myers | |
| 6,062,436 | A | * | 5/2000 | Fuchs | 222/212 |
| 6,068,617 | A | * | 5/2000 | Richmond | 604/255 |
| 6,089,272 | A | * | 7/2000 | Brand et al. | 137/859 |
| 6,537,258 | B1 | | 3/2003 | Guala | |

FOREIGN PATENT DOCUMENTS

| | | |
|---|---|---|
| WO | WO 03/018104 | 3/2003 |
| WO | WO 03/018105 | 3/2003 |

* cited by examiner

*Primary Examiner* — Stephen M Hepperle
*Assistant Examiner* — William McCalister
(74) *Attorney, Agent, or Firm* — Stein McEwen, LLP

(57) ABSTRACT

A positive pressure one way medical valve contains an inlet (10), outlet (11), an internal flow path between the inlet and the outlet and a plunger (12) movable between a retraced sealing position, where backflow is reduced or prevented and an extended open position, where fluid can flow from the inlet to the outlet. The plunger is moved from the retraced to the extended position by insertion of a tip onto the inlet (10). A variable volume chamber (23) is defined partially by an elastomeric member (14) that is stretched, when plunger is in the extended position and reduced, when the plunger is in the retraced position so to increase or decrease the volume of the chamber respectively. A valve (50), which is movable between open and closed positions by the presence or absence of fluid passing through the inlet, immediately seals the flow pathway before the plunger is retraced.

7 Claims, 13 Drawing Sheets

ONE WAY VALVE THAT USES FLUID PRESSURE TO OPEN AND CLOSE THE VALVE

FIELD OF THE INVENTION

This invention is directed to a valve that can be attached to a catheter, a needle or any other type of injecting device and that has a particular configuration to prevent backflow. The invention is particularly directed to a needle free access valve for use in a needle free intravenous access system. The invention is also particularly directed to a one-way valve to prevent backflow, and where the one-way valve contains a valve or similar device that opens, and importantly that also closes by the presence or absence of fluid flow such that the one-way valve can close and therefore prevent or reduce backflow without needing, at least initially, to move any part of the valve. The invention is also directed to a one-way valve having a plunger that does not directly contact the interior wall of the valve.

BACKGROUND ART

A needle free access valve is one where the valve can be opened using a needleless syringe. A needleless syringe is a syringe where the needle has been removed such that the front of the syringe has only the luer taper or luer lock. Such valves are known but suffer from a number of disadvantages.

A serious disadvantage with many existing one-way valves is that fluid can flow back into the valve from the body cavity or the body in which the needle etc has penetrated. This results in contamination, and a potential health hazard. Most valves are provided with some form of spring or bias to naturally bias the valve back into the closed position.

In our earlier international patent application PCT/AU02/00861 there is described a one way valve that delivers a positive pressure to prevent backflow. In this valve arrangement, there is provided a sliding plunger which is connected to a biasing web and movement of the plunger stretches and retracts the web. The web forms part of a variable volume chamber to keep a positive pressure.

One disadvantage with this valve and with most other one-way valves used in the medical area is that the valve typically contains a sliding plunger that slides between the open position and the closed position. The sliding plunger is typically biased back to the closed position. Insertion of a luer tip or other type of device into the inlet of the one-way valve pushes the sliding plunger against the bias to the open position. Therefore, the plunger cannot move to the closed position until the luer tip or other device has been removed from the inlet. Thus, when the fluid flow through the device ceases, the plunger remains in the open position (and therefore backflow is not prevented) until such time as the luer tip or other device has been removed from the inlet. This can create circumstances where a small amount of backflow can still occur, or where there is a time delay between the fluid flow ceasing, and removal of the tip or other device from the inlet of the one-way valve (which then allows the plunger to move to the closed backflow prevention position).

Therefore, there would be an advantage if it were possible to provide a one-way valve that may contain parts that move between an open position and a closed position (for instance such as described in our earlier PCT application listed above) but which can also contain some form of valve or sealing member that is operable between a open fluid flow position and a closed position by the action of fluid. An advantage of this is that as soon as the fluid flow stops, the valve can move to the closed position before any further parts of the valve move (e.g. the plunger). The valve can be in addition to the ordinarily moving parts of the one-way valve, or can replace at least some of the ordinarily moving parts of the one-way valve.

Another disadvantage with backflow prevention valves is that there is still the possibility of blood finding its way ultimately close to the inlet of the valve which can be a source of hazard. Therefore, there would be an advantage if it were possible to provide a one-way valve that could reduce or eliminate this occurrence.

OBJECT OF THE INVENTION

It is an object of the invention to provide a valve assembly for use in the medical field and which can reduce or entirely prevent the occurrence of backflow from the body cavity etc back through the valve assembly, and especially without requiring parts of the valve to slide between an open position and a closed position.

It is further object of the invention to provide a valve assembly that may at least partially overcome the abovementioned disadvantages or provide the public with a useful or commercial choice.

In one form, the invention resides in a one way valve assembly that comprises:
1. an inlet and an outlet,
2. a flow pathway that extends through the valve assembly from the inlet to the outlet,
3. a plunger that is positioned in the flow pathway and which can move between a forward open position where fluid can flow from the inlet to the outlet, and a retracted closed position where fluid flow is reduced or prevented from flowing from the inlet to the outlet,
4. an at least partially elastic web that has an outer end fixed to the valve assembly, and an inner portion which engages with the plunger such that reciprocation of the plunger from the retracted position to the forward position causes at least part of the web to stretch,
5. a variable volume chamber having walls at least partially defined by the plunger and the web, the chamber forming part of the flow pathway, the chamber having smaller or nil volume when the plunger is in the retracted position, and a larger volume when the plunger is in the extended position, whereby upon retraction of the plunger, the variable volume chamber reduces in volume which results in a pumping action to pump fluid through the fluid pathway towards the outlet, thereby reducing or preventing backflow, and
6. a valve positioned within the flow path and which is movable between an open position enabling fluid to flow towards the outlet of the valve, and a closed position preventing backflow of fluid through the inlet, characterised in that the valve is moved to the open position by the flow of fluid, and the valve is moved to the closed position by the absence of flow of fluid.

In one form, the valve may be naturally biased to the closed position and is moved to the open position by the flow of fluid and will move to the naturally closed position when the flow of fluid stops.

The one-way valve assembly will typically contain the valve as described above and may also contain a sliding plunger which may be similar to that described in our earlier PCT application. The sliding plunger is operated by insertion or removal of a tip through the inlet of the valve assembly, and the valve is operated by fluid flow.

An advantage of this arrangement is that backflow can be prevented as soon as fluid flow through the valve assembly ceases irrespective of whether the tip has been removed from or is still in the inlet of the valve assembly.

Although there is a preference to provide a one-way valve assembly containing a sliding plunger as described above, in a broad form of the invention, there may be provided a one-way valve assembly that comprises an inlet and an outlet, a variable volume chamber which increases in volume as fluid flows through the assembly from the inlet to the outlet, and which decreases in volume upon removal of a tip or similar device from the inlet, or upon slowing or stopping of fluid flow from the inlet to the outlet, the decrease in volume providing a positive pressure to reduce or to prevent backflow, and a valve which is movable between an open position where fluid can flow from the inlet to the outlet, and a closed position where backflow is reduced or prevented, the valve being movable from the closed position to the open position by fluid pressure, and being movable from the open position to the closed position upon a reduction or stopping of the fluid pressure.

With this arrangement, the valve apparatus can be attached to a syringe (or other device), and a needle, catheter or other body-injecting device can be attached to the apparatus. The contents of the syringe can then be passed through the apparatus and into the body by depressing the plunger into the forward (open) position. As the plunger moves towards the forward position, it stretches at least part of the web and the variable volume chamber adopts the larger volume. However once the syringe is removed, or retracted, the web retracts to its initial position, causing the plunger to be pushed back into the closed position and at the same time contracting the variable volume chamber. The contraction causes a positive pressure inside the apparatus that means that backflow does not occur. Indeed, it is found that the positive pressure is sufficient to at least partially "pump" any residual fluid in the apparatus through the outlet upon retraction of the plunger. This is in contrast to known devices where retraction of the plunger or closure of the valve often allows backflow of fluid through the outlet and into the valve apparatus.

In addition, the valve assembly contains the valve that is operated by the fluid flow and not by any insertion or removal of a luer tip etc into the valve assembly. Thus, as soon as the fluid in the syringe stops flowing through the valve assembly, this particular valve will move to the closed position even when the plunger is still in the open position.

The valve assembly may have features similar to or identical with those described in our above referenced PCT application, and therefore may have an outer body formed in two parts that are attached together. The two parts may comprise a top part, and a base part. The top part is substantially hollow and suitably contains an outer passageway of smaller diameter or cross-section, and an inner passageway of larger diameter or cross-section, the inner passageway forming part of an internal chamber.

The base part may be substantially hollow and may contain an outer passageway of smaller diameter or cross-section, and an inner passageway of larger cross-section or diameter and which forms part of the internal chamber that is also defined by the top part. Thus, when the two parts are attached, there is provided a substantially central internal chamber. The outer passageway of the base part may be surrounded by attachments to allow the outlet to attach to a needle etc.

The apparatus has a flow pathway that extends through the valve assembly from the inlet to the outlet, and typically through the central internal chamber described above.

The apparatus may contain a plunger. The plunger, if present, is moveable between a forward open position where the plunger moves more towards the outlet, and a retracted closed position where the plunger is more towards the inlet. The plunger typically slides or reciprocates between the two positions.

The plunger has a forward portion which is typically a projecting nose portion. Suitably, the plunger also has a rear body portion. The nose portion and the body portion may be formed integrally. The plunger suitably has a fluid flow pathway extending at least partially therethrough. The fluid flow pathway may comprise an internal flow passageway extending through the nose portion which means that the nose portion may have an opening. Suitably, the internal flow passageway includes a transverse through bore in the plunger such that fluid can pass through the through bore and through the flow passageway that extends through the nose portion.

The rear body portion of the plunger is typically configured and dimensioned to substantially fill the outer passageway in the top part of the valve assembly. The rear body portion typically has a sealing face extending about the rear body adjacent the end face and which seals with the internal wall of the outer passageway.

The plunger may have an engagement means to engage with the elastic web. The engagement means may comprise an annular step or shoulder portion on the plunger and which can catch against or engage with the elastic web upon forward movement of the plunger. Alternatively, the plunger can push against the web.

The apparatus has an at least partially elastic biasing web/diaphragm or "sock". The web may be formed of a rubbery elastic material having a good memory. In one form of the invention, the web may be formed as a separate component. The elastic web may be substantially circular with an opening through which part of the plunger can project. The web may have a peripheral edge that is held against movement in the valve assembly. Suitably, the peripheral edge also comprises a sealing edge. Preferably, the web is elastic and can therefore be stretched upon forward movement of the plunger.

The web may have an internal opening, which is typically a central opening and through which part of the plunger can pass, which is typically a nose portion of the plunger. If desired, the plunger may be provided with an annular recess to capture the wall of the internal opening. With this arrangement, the plunger may be provided with seals.

It is envisaged that the plunger and the web can be formed integrally.

The valve that forms part of the valve assembly and which is operated by fluid flow may have various configurations and may be attached in various places in the valve assembly, but will typically be positioned to intercept the fluid flow. It is envisaged that the valve will be positioned in the inlet area of the valve assembly, and will usually be positioned between the inlet and the variable volume chamber.

In one form of the invention, the valve may be attached relative to the plunger such that the valve moves as the plunger moves.

However, in another form of the invention, the valve may be attached to part of the assembly other than the plunger such that the valve does not slide or move with the plunger. In this form of the invention, the valve may be formed separately and fitted to the remainder of the valve assembly, or may be formed integrally with a part of the valve assembly.

It is preferred that the valve comprises at least one member that can move, typically by flexing or expanding or bending between the open position and the closed position. For this reason, it is preferred that the valve contains a resilient portion or consists essentially of a resilient member.

It is preferred that the valve is positioned in the fluid flow pathway such that when the valve is not subjected to the force of fluid flow, the valve adopts the closed position where its seals the fluid flow pathway. However, when subjected to the force of fluid flow, the valve can move to the open position.

It is preferred that the valve is manufactured from material, or otherwise made such that it naturally adopts the closed position, such that when the fluid flow stops, the valve will move naturally to the closed position without requiring any further actuating force on the valve. In one form, the valve can be made from a plastic material or a rubber material, or an elastomeric material which will return to a rest (sealing) position when the fluid flow force stops. The material may comprise a silicone material, a polyethylene, a polyvinyl chloride, nylon, other types of homopolymers and copolymers, and the like. The material may also comprise a metal such as thin spring steel. It is also envisaged that the valve can be made of composite materials, laminated materials and the like.

The assembly will typically contain at least one valve of this design, but it is envisaged that there may be circumstances where two or more of such valves would be desirable. For instance, under instances of high back pressure, there may be an advantage in providing more than one valve.

The valve may have various different designs. The valve may be disk like or planar and may be circular when viewed in plan (typically if the fluid pathway in this area is circular). However, the valve may have other shapes such as oval, rectangular, triangular, tubular, and the like. The valve may have a diameter or cross-section which will depend on the size of the fluid flow pathway, but for a one-way valve of typical size, it is envisaged that the valve will have a diameter or cross-section size of between 3-25 mm. The thickness of the valve will also depend on the material and it is envisaged that the valve will have a thickness of between 0.5-5 millimeters and typically between 0.5-3 millimeters. Of course, no particular limitation should be placed on the invention merely by the provision of these dimensions which have been given for illustrative purposes only.

The valve may be attached to or relative to the plunger, and will typically be attached to or relative to the part of the plunger that is adjacent the inlet of the valve assembly.

This part of the plunger can be called the "base part". In one form, the valve may comprise a disk like member attached to the front of the base part of the plunger. The disk like member may be spaced slightly forward of the plunger by at least one spacing member and against a central part of the valve. The valve is preferably made from resilient material and the peripheral part of the valve is not supported and can therefore flex. The valve can be positioned adjacent an internal wall of the fluid flow pathway such that the valve will naturally adopt a sealing position to seal the fluid flow pathway, but the peripheral part of the valve can flex away from the sealing position (and therefore to the open position) upon the force of fluid passing through the inlet. In this form of the invention, it is preferred that the valve is positioned such that when a luer tip of a syringe is inserted into the inlet of the valve assembly, it will press against the valve. This can further assist in the sealing process and will be described in greater detail below.

In another form the valve may be attached to the end of the plunger, and typically to the end that is adjacent the inlet of the valve assembly. In this form, the plunger may contain a flow passageway, and the valve extends over the flow passageway. The valve may be formed from elastomeric or resilient material and will typically contain a small opening extending through the valve body. When the valve is in the "rest" or natural position, the small opening is squeezed closed, or otherwise closed. However, when fluid pressure is applied to the valve, the valve will flex and this will cause the small opening to open thereby allowing fluid to pass through the valve assembly. However, as soon as the fluid flow stops, the valve will move back to the rest or natural position which will squeeze the opening to the closed position.

In another form, the valve is not attached to the plunger, but is instead attached to a different part of the valve assembly. In this particular form of the invention, the valve may comprise a tubular sleeve which can stretch under the force of fluid. The tubular sleeve can be positioned inside the fluid flow passageway and in such a position that the sleeve is in a natural sealing position where its seals against the plunger, but the force of fluid will cause the tubular sleeve to expand or move to enable fluid to pass through the valve assembly.

In a modification of the form of the invention described immediately above, the sleeve may be tubular but instead of being entirely stretchable, the sleeve may comprise a "split sleeve" that can open up to enable fluid to flow through the valve assembly but which will naturally adopt a closed position where the split in the sleeve is closed. In a modification to this form of the invention, the sleeve may comprise a portion that is rigid and a portion that is stretchable to enable the sleeve to move between the open position and the closed position.

In another form of the invention, and in which an embodiment is described as the "sixth" embodiment, and illustrated in FIGS. 22-24, there is provided a positive pressure one way valve assembly that comprises:

1. An inlet and an outlet,
2. A flow pathway that extends through the valve assembly from the inlet to the outlet,
3. A plunger that is positioned in the flow pathway and which can move between a forward open position where fluid can flow from the inlet to the outlet, and a retracted closed position where fluid is prevented from flowing from the inlet to the outlet, the plunger having a forward portion,
4. An at least partially elastic web that has an outer end fixed to the valve assembly, and an inner portion which engages with the plunger such that reciprocation of the plunger from the retracted position to the forward position causes at least part of the web to stretch,
5. A variable volume chamber having walls defined by the plunger and the web, the chamber forming part of the flow pathway, the chamber having smaller or nil volume when the plunger is in the retracted position, and a larger volume when the plunger is in the extended position, whereby upon retraction of the plunger, the variable volume chamber reduces in volume which results in a pumping action to pump fluid through the fluid pathway towards the outlet, thereby reducing or preventing backflow, and
6. An annular seal on the piston and which seals against an internal wall of the valve when the piston is in the retracted position to seal off the variable volume chamber such that the variable volume chamber does not form part of the flow pathway.

With this arrangement, the apparatus can be attached to a syringe (or other device), and a needle, catheter or other body-injecting device can be attached to the apparatus. The contents of the syringe can then be passed through the apparatus and into the body by depressing the plunger into the forward (open) position. As the plunger moves towards the forward position, it stretches at least part of the web and the variable volume chamber adopts the larger volume. However once the syringe is removed, or retracted, the web retracts to its initial position, causing the plunger to be pushed back into the closed position and at the same time contracting the variable volume chamber. The contraction causes a positive pressure inside the apparatus that means that backflow does not occur. Indeed, it is found that the positive pressure is sufficient to at least partially "pump" any residual fluid in the apparatus through the outlet upon retraction of the plunger. This is in contrast to known devices where retraction of the plunger or closure of the valve often allows backflow of fluid through the outlet and into the valve apparatus.

The valve assembly may have an outer body formed in two parts that are attached together. The two parts may comprise a top part, and a base part. The top part is substantially hollow and suitably contains an outer passageway of smaller diameter or cross-section, and an inner passageway of larger diameter or cross-section, the inner passageway forming part of an internal chamber. The outer passageway may contain longitudinal slots or recesses that comprise fluid ports the reason for which will be described in greater detail below.

The base part may be substantially hollow and may contain an outer passageway of smaller diameter or cross-section, and an inner passageway of larger cross-section or diameter and which forms part of the internal chamber that is also defined by the top part. Thus, when the two parts are attached, there is provided a substantially central internal chamber. The outer passageway of the base part may be surrounded by attachments to allow the outlet to attach to a needle etc.

The apparatus has a flow pathway that extends through the valve assembly from the inlet to the outlet, and typically through the central internal chamber described above.

The apparatus has a plunger. The plunger is moveable between a forward open position where the plunger moves more towards the outlet, and a retracted closed position where the plunger is more towards the inlet. The plunger typically slides or reciprocates between the two positions.

The plunger has a forward portion which is typically a projecting nose portion. Suitably, the plunger also has a rear body portion. The nose portion and the body portion may be formed integrally. The plunger suitably has a fluid flow pathway extending at least partially therethrough. The fluid flow pathway may comprise an internal flow passageway extending through the nose portion which means that the nose portion may have an open outer end. Suitably, the internal flow passageway includes a transverse through bore in the rear body portion such that fluid can pass through the through bore and through the flow passageway that extends through the nose portion.

The rear body portion of the plunger is typically configured and dimensioned to substantially fill the outer passageway in the top part of the valve assembly. Suitably, the rear body portion has an end face that is substantially flush with the end of the top part of the valve assembly that can make cleaning of this area quite easy. The rear body portion typically has a sealing face extending about the rear body adjacent the end face and which seals with the internal wall of the outer passageway.

The plunger may have an engagement means to engage with the elastic web. The engagement means may comprise an annular step or shoulder portion on the plunger and which can catch against or engage with the elastic web upon forward movement of the plunger. Alternatively, the plunger can push against the web.

The apparatus has an at least partially elastic biasing web or "sock". The web may be formed of a rubbery elastic material having a good memory. In one form of the invention, the web may be formed as a separate component. The elastic web may be substantially circular with an opening through which part of the piston can project.

The web may have a peripheral edge that is held against movement in the valve assembly. Suitably, the peripheral edge also comprises a sealing edge. Preferably, the web is elastic and can therefore be stretched upon forward movement of the plunger.

The web may have an internal opening, which is typically a central opening and through which part of the plunger can pass, which is typically a nose portion of the plunger. If desired, the plunger may be provided with an annular recess to capture the wall of the internal opening. With this arrangement, the plunger may be provided with seals.

It is envisaged that the plunger and the web can be formed integrally.

BRIEF DESCRIPTION OF THE DRAWINGS

Embodiments of the invention will be described with reference to the following drawings in which.

BEST MODE

Figure 2:
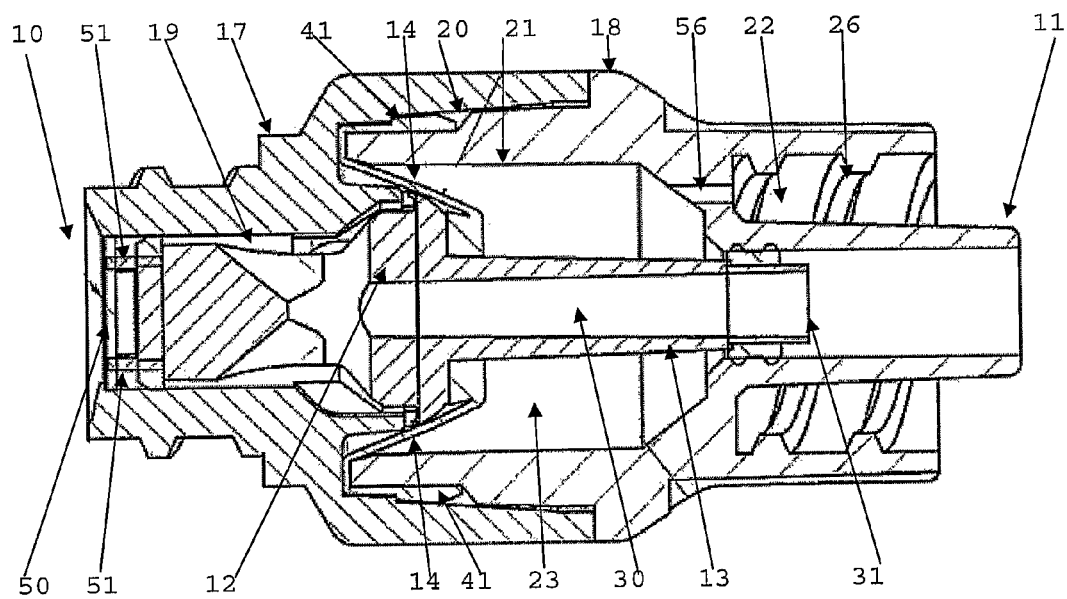
FIGS. 2-4. Illustrate a first embodiment of the invention which comprises a valve assembly that contains a valve attached to the end of the plunger and which can flex between an open position and a closed position.
Figure 3:
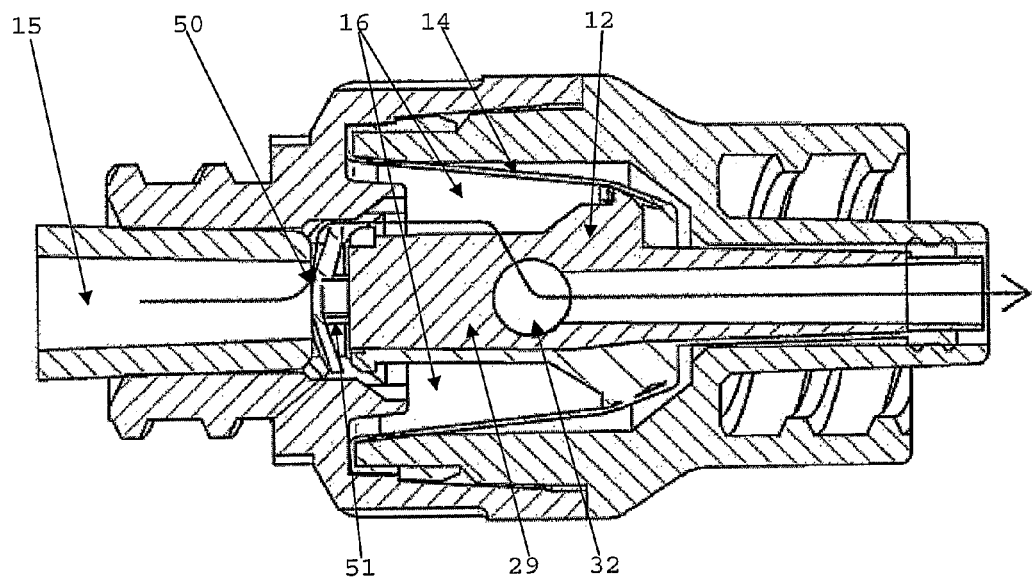
Figure 4:
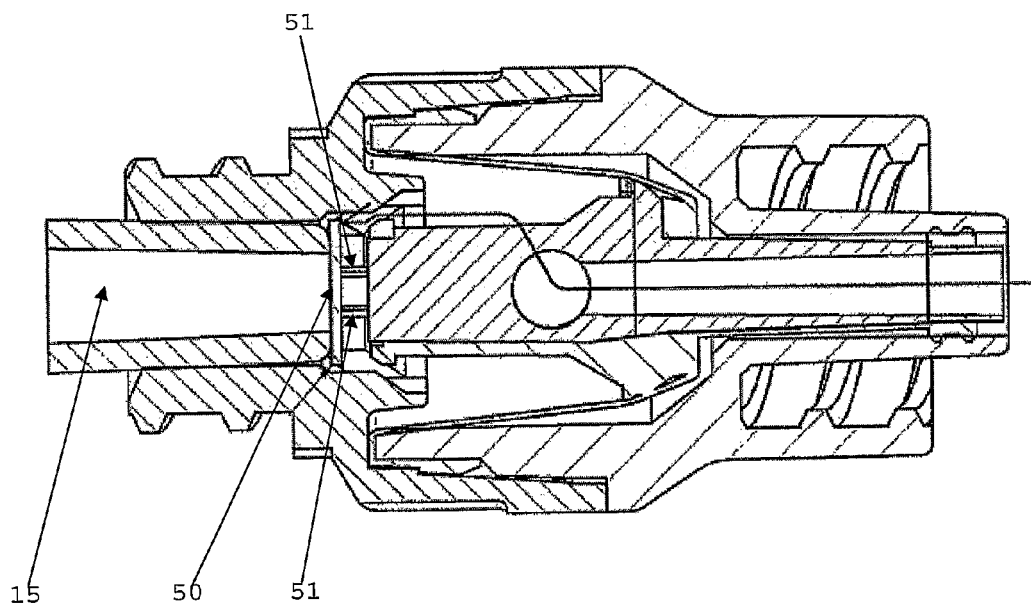

Referring to the drawings, and initially to FIG. 2, there is illustrated a valve assembly which comprises an inlet 10 and an outlet 11, a flow pathway that extends through the valve assembly from inlet 10 to outlet 11, a plunger 12 that is positioned in the flow pathway and which can reciprocate between a pushed forward open position illustrated in FIGS. 3 and 4, and a retracted closed position illustrated in FIG. 2, an elastic web 14 which extends about plunger 12, and a variable volume chamber 16 (see FIG. 3) which is larger in FIGS. 3 and 4 and smaller or nil in FIG. 2.

Referring to the parts in greater detail, the valve assembly in the embodiment comprises an outer body that is formed of two parts that are attached together, the two parts being a first (top) part 17 and a second (base) part 18. These parts are formed of plastic material and are joined together by any suitable method. Part 17 is substantially hollow. Part 17 comprises an outer passageway 19 which is circular and which has a smaller diameter, and an inner passageway 20 which is also circular and which has a substantially larger diameter. Similarly, part 18 has an inner passageway 21 that has a substantially larger diameter than outer passageway 22. When the two parts are joined, the two larger diameter passageways together form an internal chamber 23. Outer passageway 22 terminates in outlet 11, while outer passageway 19 terminates in inlet 10.

Part 18 contains a standard luer lock fitting 26 which extends about passageway 22 and which functions to allow a needle etc to be attached to this part of the assembly. Of course, other types of attachments can also be used.

Inner passageway 21 has a diameter that is smaller than inner passageway 20. Thus, the wall of inner passageway 21 passes into inner passageway 20 this being best illustrated in FIG. 2. Moreover, the wall has a length that results in the wall being spaced somewhat from wall of top part 17 (see FIG. 2). This spacing facilitates the attachment of the elastic web that will be described in greater detail below.

Plunger 12 is formed of plastic material and comprises a unitary body. The plunger has a particular configuration that provides a nose portion 13, and a rear body portion 29 (best illustrated in FIG. 3). Nose portion 13 is slightly tapered and has a through passageway 30 which passes through an open outer end 31 and functions to allow fluid to flow through the valve assembly. Body portion 29 is provided with a transverse through bore 32 through which fluid can pass. Body portion 29 has a substantially cylindrical outer wall.

When plunger 12 is pushed forwardly from the position illustrated in FIG. 2 to the position illustrated in FIG. 3, the plunger only moves by a few millimeters, but this movement is sufficient to allow fluid to pass along the outside wall of body portion 29, through bore 32 through passageway 30 and through outlet 11. Conversely, when the plunger is retracted from the position illustrated in FIG. 3 to the position illustrated in FIG. 2 the plunger again seals against passage of fluid from inlet 10 through outlet 11.

The plunger is biased back to its retracted position by the elastic web 14 which also provide additional functions. Elastic web 14 is made of a rubbery elastic material having an excellent memory. The elastic web is substantially circular and has a base peripheral edge 41 that is thickened with respect to the thickness of the portion immediately next to the peripheral edge. The thickened peripheral edge 41 is trapped between the wall of part 18 and the inner wall of part 17. Peripheral edge 41 also functions to seal the fluid pathway in the apparatus.

As the plunger 12 is pushed to the forward open position, it will stretch the biasing web 14 which forms part of the variable volume chamber 16 and the movement will increase the volume of chamber 16. When the plunger is retracted to the closed position (and web 14 forms part of a biasing means to bias the plunger back to the closed position), the variable volume chamber will reduce in volume and will provide a positive pressure in the valve to prevent backflow of any fluid into outlet 11.

The web is designed such that when the plunger 12 is in the retracted closed position, there is still some tension in the web to keep the plunger in the retracted position.

A small air passageway 56 is provided to allow air to pass into chamber 23 upon shrinking of the web and to allow air to pass out of chamber 23 upon stretching of the web.

The valve assembly prevents back flow of fluids by maintaining a positive pressure in chamber 16.

Another advantage with the arrangement is that possibly contaminated air is kept separate from the fluid flow pathway of the valve assembly by virtue of the web 14 and the various seals.

The arrangement described above is similar to that described in our earlier international patent application, and has been repeated merely to describe the main part of the valve assembly.

However, one disadvantage with the arrangement described above is that the valve assembly can only seal once the plunger 12 has been retracted. As the plunger 12 cannot be retracted unless the tip 15 (see FIG. 3) has been pulled out of inlet 10, the valve assembly suffers from a disadvantage that if the fluid flow through tip 15 stops, the valve assembly remains in the "open" position as the plunger 12 is still in the pushed forward open position by virtue of tip 15.

The present invention is directed to a modification of the above valve assembly that enables the valve assembly to prevent backflow even when the plunger is in the pushed forward open position.

Figure 5:
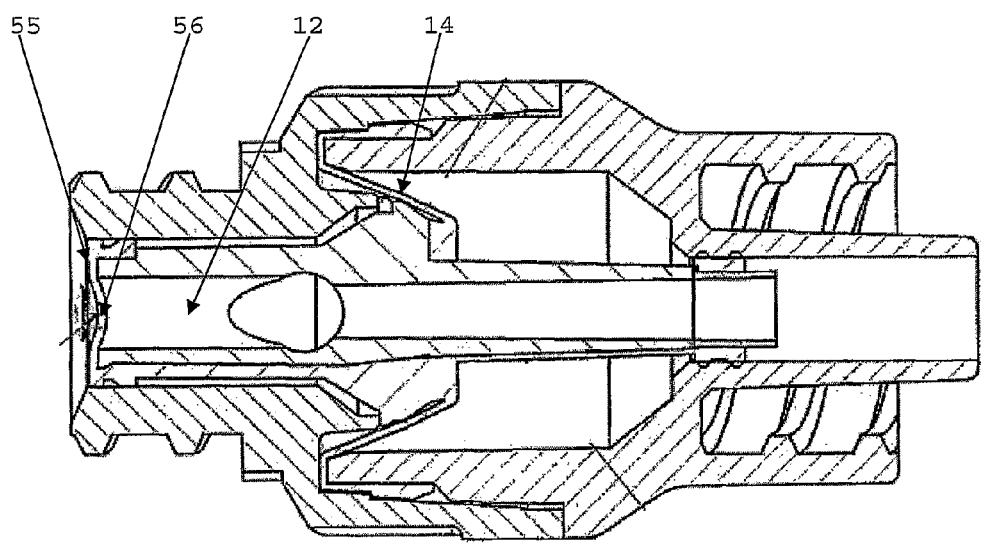
FIGS. 5-7. Illustrate a second embodiment of the invention which comprises a valve which is also positioned over the end of the plunger but which contains an opening extending through the valve and which can open or close.
Figure 6:
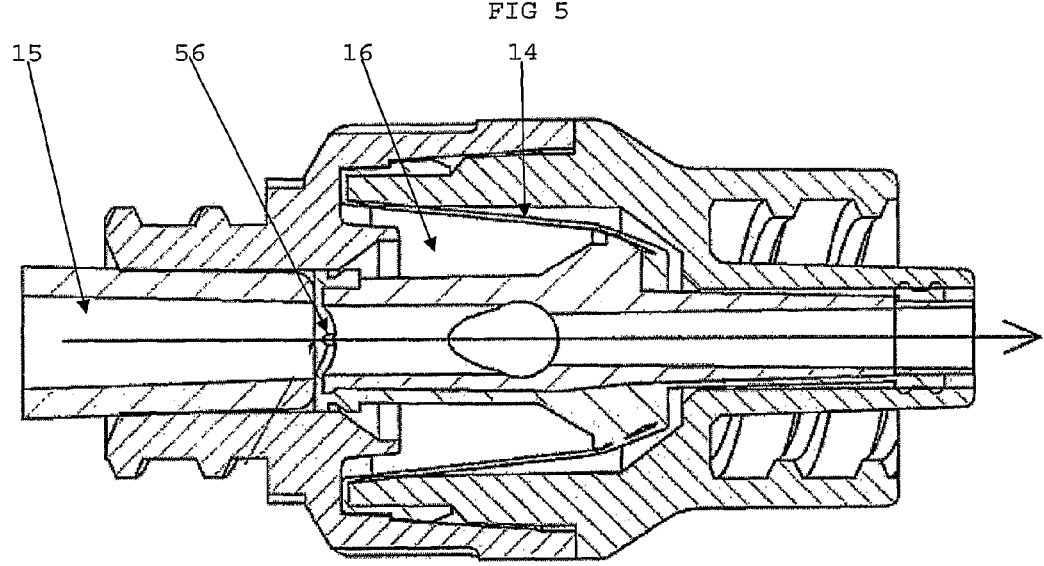
Figure 7:
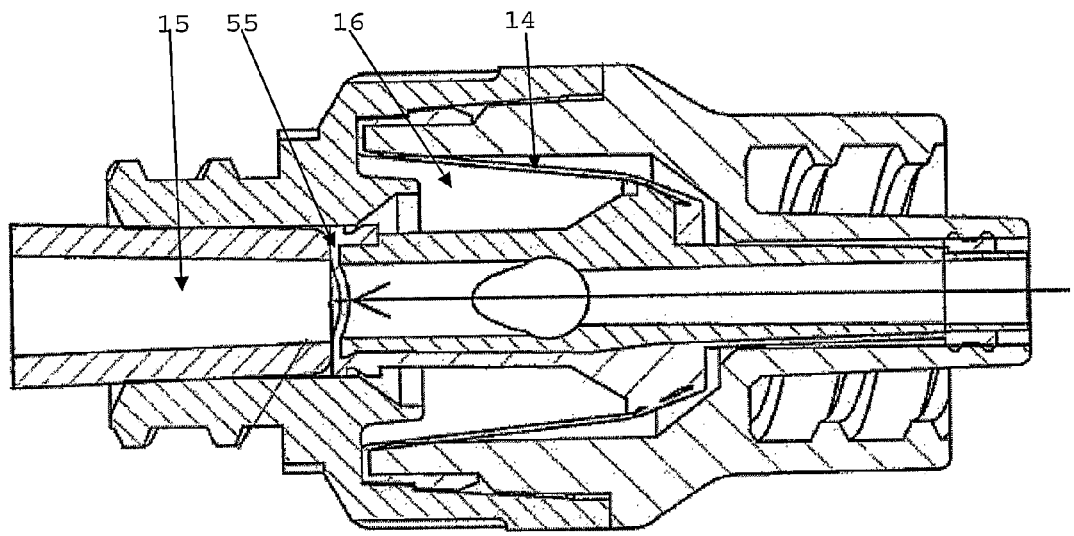
Figure 8:
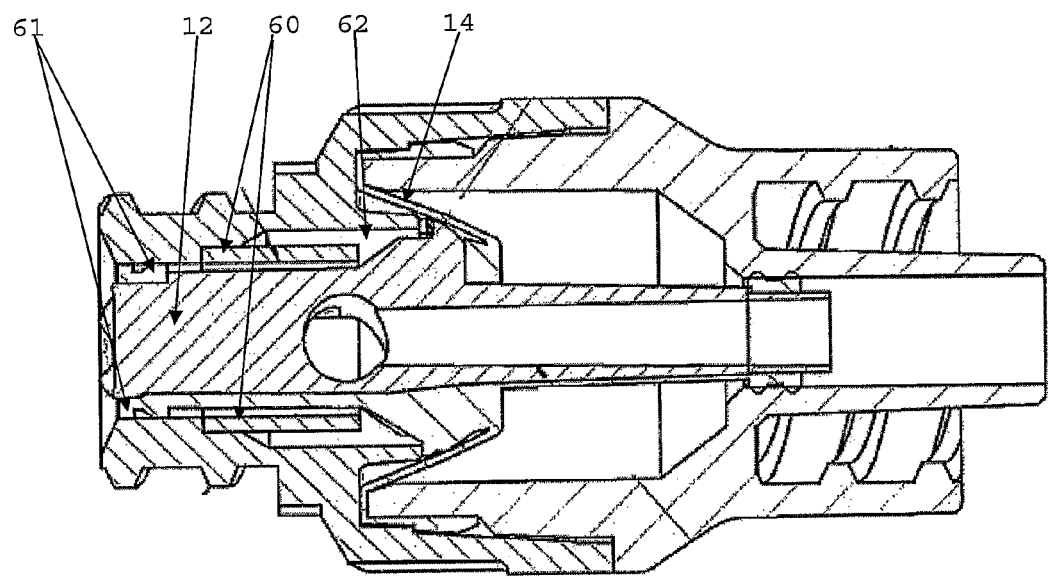
FIGS. 8-10. Illustrate a third embodiment of the invention which comprises a valve of tubular design that is not attached to the plunger but is instead attached to the internal wall of the valve assembly.
Figure 9:
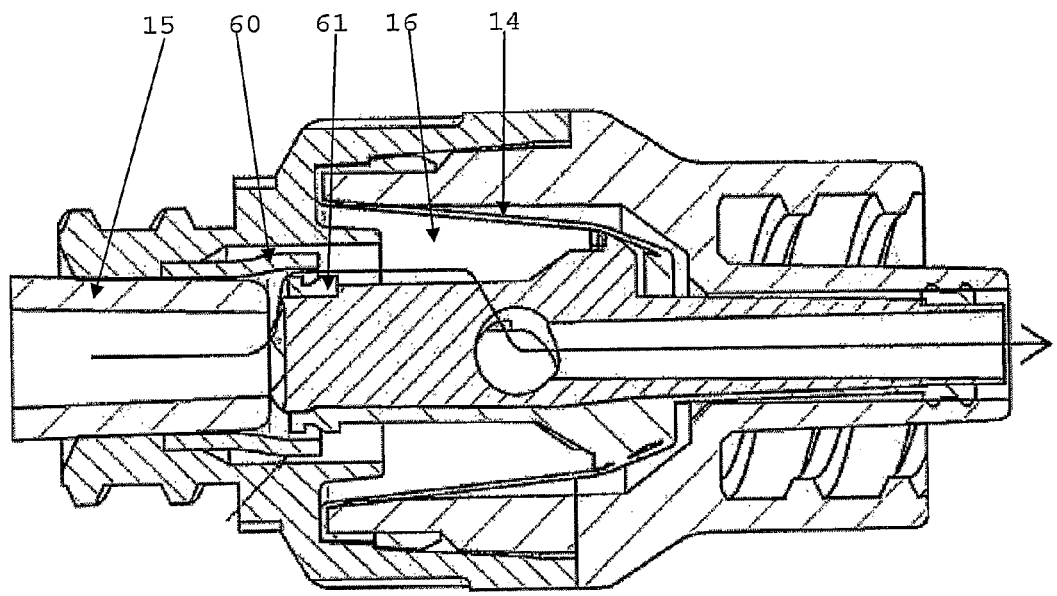
Figure 10:
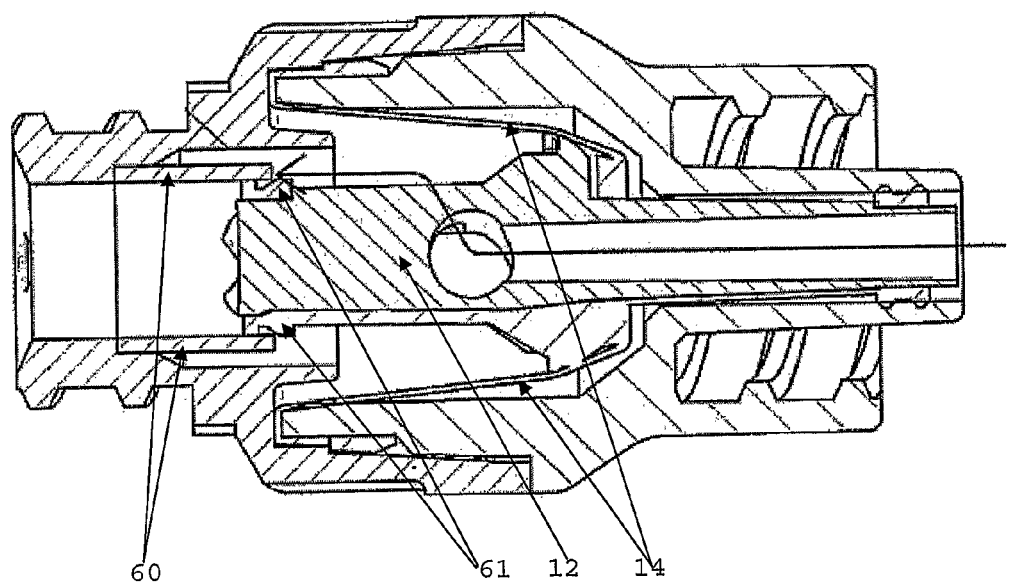

FIGS. 2-4 illustrate the first embodiment that enables this to happen. FIGS. 5-7 illustrate a second embodiment. FIGS. 8-10 illustrate a third embodiment that enables this to happen, and FIGS. 11-15 illustrate a fourth embodiment. Of course, the invention should not be limited to the precise description of the embodiments, and should be extend to the general concept of providing a valve assembly that can prevent back pressure as soon as the fluid flow stops.

Figure 1:
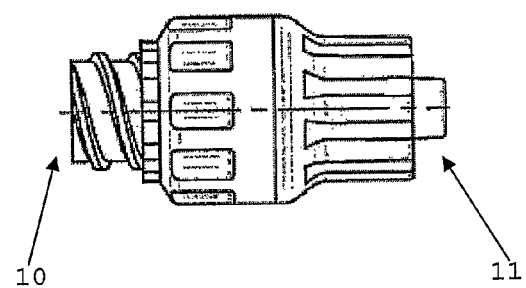
FIG. 1. Illustrates a typical design of a one-way valve assembly according to an embodiment of the invention.

Referring initially to FIG. 1, this is a general view of the outside of the valve assembly and shows the inlet 10 and the outlet 11.

Referring to FIGS. 2-4, the general parts of the valve assembly have been described above. However, a modification is in the provision of an end valve 50 which is fitted to the end of plunger 12 that is positioned adjacent inlet 10. That is, valve 50 is the "first point of contact" with a tip 15. In this particular embodiment, the valve 50 comprises a substantially circular flat disk which is made of resilient or bendable material. The valve is supported by a pair of spacing members 51 that are attached to plunger 12 and that space the valve a few millimeters in front of plunger 12. The spacing members hold the central part of the valve relatively rigid, but it can be seen that the spacing members are spaced inwardly from the peripheral edge of the valve. This means that the peripheral edge of the valve is not supported by the spacing members 51 and can flex inwardly. The flexing function causes the valve to move to the open position enabling fluid to flow through tip 15 and through the remainder of the valve assembly in a manner described above. Thus, referring to FIG. 2, the valve 50 is in the closed position where the valve is planar. A tip 15 (see FIG. 3) can be inserted through inlet 10 and pushed into the valve assembly. As this happens, plunger 12 will be moved forwardly to enlarge the variable volume chamber 16. Also, the tip pushes against valve 10. At this stage though and until fluid flows through tip 15, valve 50 remains in the closed position illustrated in FIG. 4. That is, valve 50 does not flex and remains in a substantially planar configuration.

As soon as fluid flows through tip 15, the fluid force will cause the peripheral edge of valve 50 to flex inwardly (see FIG. 3) which now moves the valve to the open position and enables fluid to flow through the variable volume chamber 16, through the transverse bore 32, and ultimately through outlet 11.

However, as soon as the fluid flow stops, the valve 50 will immediately return or flex back to the flat or planar configuration (see FIG. 4) which will immediately prevent fluid from flowing in the reverse direction. It can be seen though that the plunger 12 is still in the forward "open" position. Also, in this position, valve 50 seals against the front of tip 15.

As the tip 15 is pulled out of inlet 10, the plunger 12 will move back to the retracted position which will reduce the size of the variable volume chamber 16 to create a positive pressure to pump out any remaining fluid through outlet 11, and to therefore prevent any backflow. However, during this process, valve 50 is closed, which means that it seals against back pressure as well.

Thus, the provision of valve 50 will cause immediate sealing of the valve assembly even when the plunger 12 is in the forward open position, as soon as fluid flow stops. There is now no longer a requirement to have the additional retraction steps of plunger 12 to create the seal. Although it is preferred that the plunger also provides a seal, it is envisaged that the plunger can also function merely to expand and retract the variable volume chamber 16, and that the primary sealing is now carried out by valve 50.

The remaining embodiments show further variations to this principle of providing a seal immediately upon stopping of fluid flow.

Referring to FIGS. 5-7, there is illustrated a valve 55. In this embodiment, the plunger 12 is of a different design and is substantially hollow to enable fluid to flow through the plunger. However, fluid flow is prevented by valve 55 that functions as an end cap and which is attached over the otherwise open end of the plunger. The valve 55 is again flexible but is naturally biased to the position illustrated in FIG. 5. Valve 55 contains a small central opening 56 which is illustrated best in FIG. 6. The central opening 56 opens only when the valve 55 is bowed inwardly. Valve 55 moves from the naturally closed position illustrated in FIGS. 5 and 7, to the open position where opening 56 is open and which is illustrated in FIG. 5, by the force of fluid passing through tip 15. Thus, as tip 15 passes through inlet 10 (see FIG. 6) it will push against plunger 12 and move plunger 12 to the forward position which expands the variable volume chamber 16. At this stage however it is important to note that valve 55 is still in the closed position illustrated in FIG. 7 and in FIG. 5. The valve will not move to the open position until fluid passes through tip 15 as the fluid pressure will cause valve 55 to bow inwardly (see FIG. 6) to open up opening 56. As soon as fluid stops flowing through tip 15, valve 55 will immediately return to the rest position (FIG. 7) which will close the opening 56. Again, the plunger 12 is still in the forward position.

The tip 15 can then be withdrawn from inlet 10 and this will cause the plunger to be pulled back to the retracted position by the elastic web 14, and in the process reducing the size of the variable volume chamber, creating a positive back pressure flow, thereby preventing back pressure. During this process, the valve 55 remains in the closed position.

FIGS. 8-10 illustrates another variation to this general principle. In this variation, a tubular valve 60 is provided. The tubular valve 60 is not attached to the plunger 12 (as is the case with the previous embodiments), but is instead attached to the inside wall of the flow passageway and adjacent the inlet 10. The tubular valve 60 is made of elastic material which means that it can be stretched to a large opening, but the natural position of the tubular valve is a shrunk position. The valve 60 has a diameter which enables the plunger 12 to slide through the valve between the plunger retracted position illustrated in FIG. 8, and the plunger extended position illustrated in FIGS. 9-10. The plunger 12 in this particular embodiment contains a peripheral seal 61 that closes the flow passageway. Thus, when the plunger is in the retracted position illustrated in FIG. 8, the valve assembly is closed. A tip 15 can be inserted through the inlet (see FIG. 9) and this causes the plunger 12 to be pushed forwardly until the peripheral seal 61 is no longer in sealing engagement with the inside wall adjacent the inlet 10. Instead, the peripheral seal 61 has moved to an enlarged portion 62 where there is no longer a sealing engagement. However, in this position, the tubular valve 60 seals against the peripheral seal 61 and therefore the flow passageway is still closed, because of the engagement of tubular valve 60 against seal 61. This particular position is illustrated in FIG. 10.

As soon as fluid flows through tip 15, the force of the fluid is sufficient to stretch the end of valve 60. This, in turn, releases the sealing engagement with valve 60 against seal 61 which means that fluid can now flow through the valve assembly. This is illustrated in FIG. 9. Thus, as long as fluid flows through tip 15, the valve 60 is forced into the stretched and open position. As soon as fluid stops flowing, valve 60 snaps to the shut position which is illustrated in FIG. 10, even though the plunger 12 is still in the pushed forward position. The plunger 12 will move back to the retracted position but only when tip 15 is removed from the valve assembly, and this will also cause the variable volume chamber 16 to shrink in volume and therefore create a positive pressure to prevent backflow.

Figure 11:
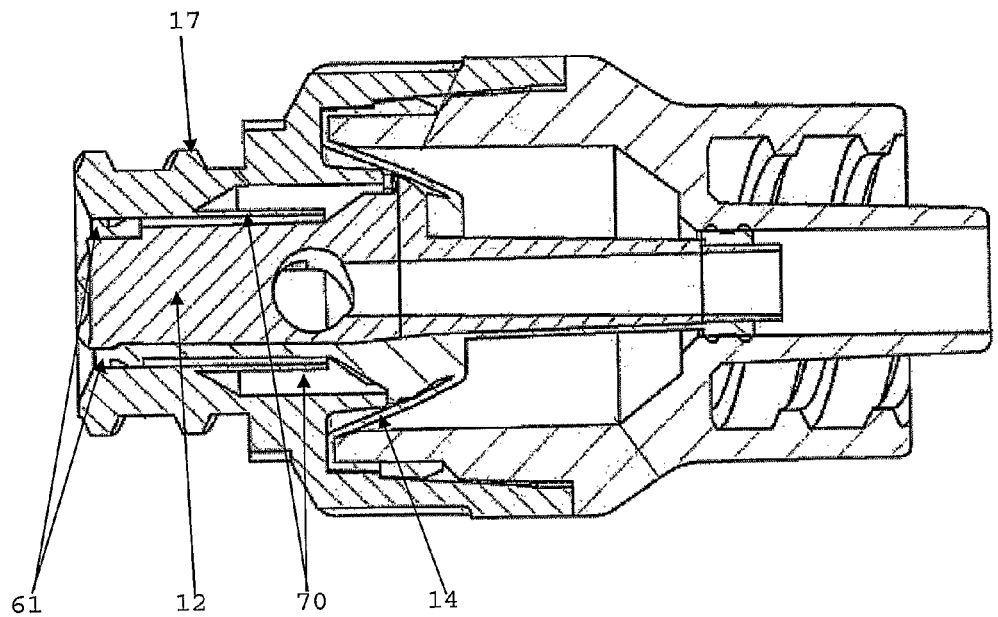
FIGS. 11-13. Illustrate a fourth embodiment of the invention which comprises a valve of tubular design, but where the valve is not a separate item but has instead been co-moulded with part of the valve housing.
Figure 12:
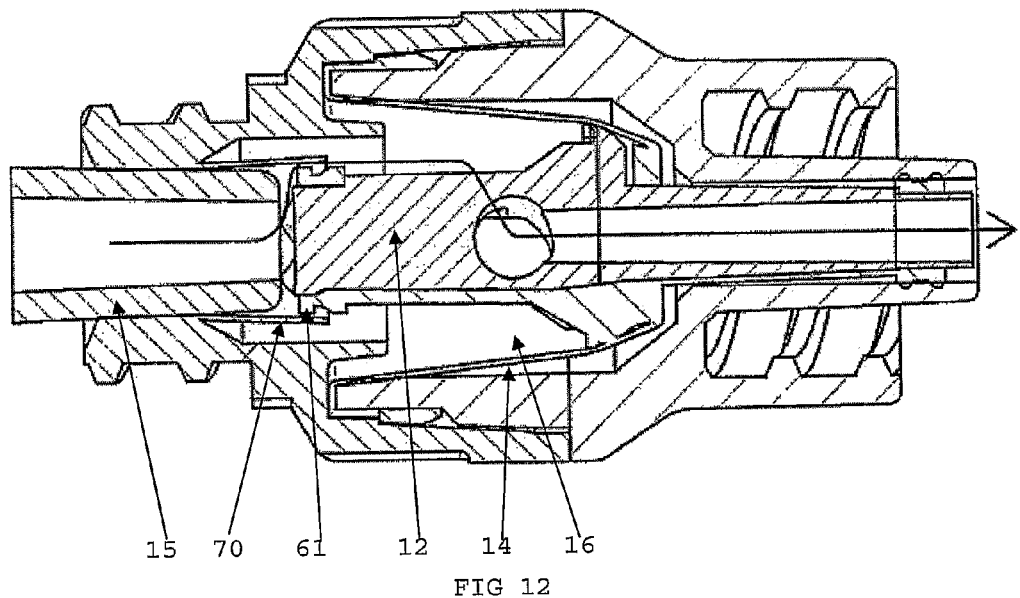
Figure 13:
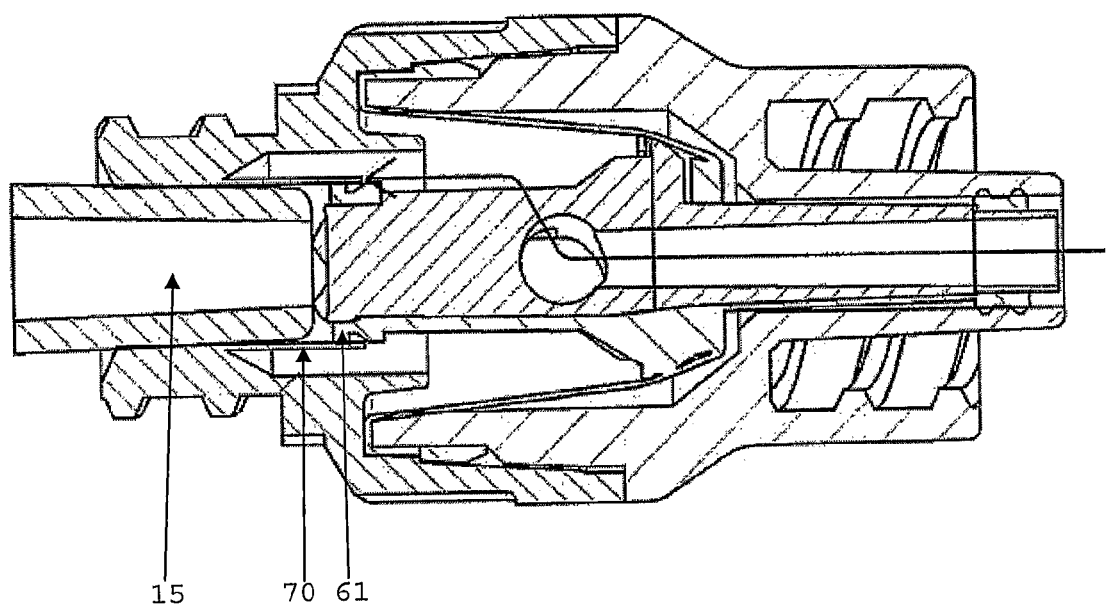

FIGS. 11-13 illustrate another embodiment of the invention which is similar to that described with reference to FIGS. 8-10 in that the valve is not attached to the plunger. In this particular embodiment, there is provided a valve 70 which is not formed separately (as is the case in FIGS. 8-10) but which is part of the first part 17 and is extruded as a unitary structure. The valve 70 again engages with the peripheral seal 61 of plunger 12 to prevent fluid flow, and the valve can again move to the open position illustrated in FIG. 12 upon flow of fluid through tip 15. As valve 70 is formed integrally with first part 17, the valve may not be formed of stretchable material. Thus, in this embodiment, the valve may be a "reed" type of valve where the tubular body contains a section separated from the remainder of the tubular body like a line. When the valve is in the closed position, the cut lines are sealed. However, when fluid flows through tip 15, the tubular body expands and the cut lines enlarge. Again, as soon as fluid stops flowing, the valve moves to the closed position without any movement of the plunger.

Referring to FIGS. 14-21, this illustrates a fifth embodiment of the invention. In this embodiment, the valve assembly is slightly modified to reduce or eliminate bio fluids (e.g. blood) flowing over the inlet of the valve assembly. The valve assembly is similar to that described above in that it comprises two parts 80, 81 that are connected together. Part 80 contains the inlet 82 and part 81 contains the outlet 83. A plunger 84 moves through the valve in a manner similar to that described previously, and the valve assembly contains a variable volume chamber defined, in part, by the resilient web 85. Plunger 84 contains a forward portion 86 containing an end face 87. In this portion is provided an annular seat 88 that extends around this part of the plunger.

One slight disadvantage with this type of valve assembly is that upon retraction of the plunger from the forward (open) position to the retracted (closed) position, some blood can pass over end face 87 which can be a source of contamination. The fifth embodiment of the invention provides a means to reduce or eliminate this.

Figure 14:
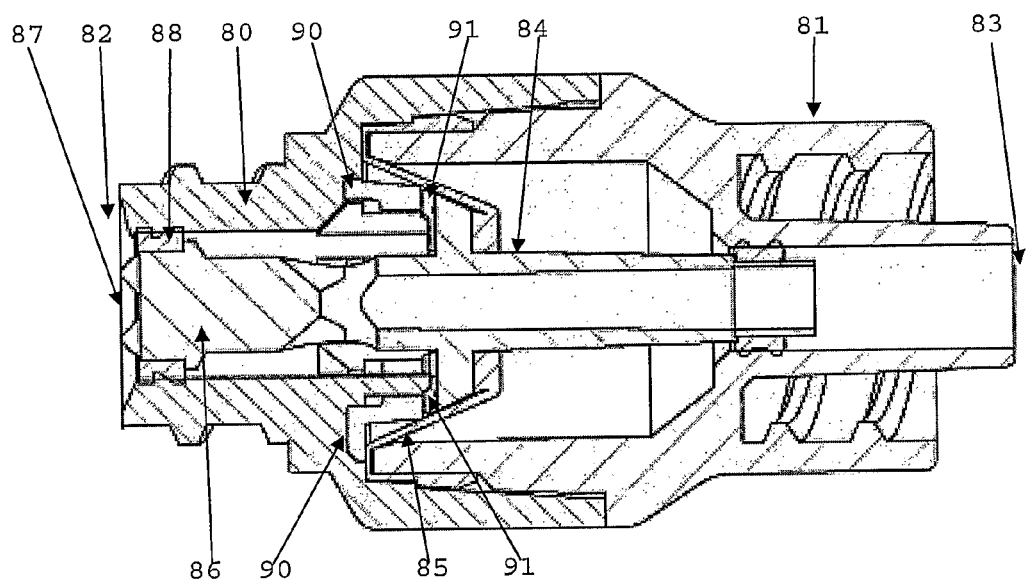
FIGS. 14-21. Illustrate a fifth embodiment of the invention which includes a flexible collar.
Figure 15:
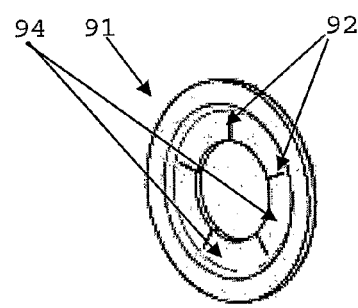
Figure 15:
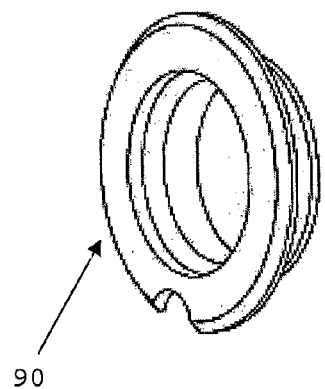

In this embodiment, the valve assembly contains one an additional part that is illustrated in FIG. 15 and which comprises a plastic (typically polypropylene) base 90 containing an elastomer collar 91 overmoulded onto base 90. Collar 91 contains a plurality of slits 92 to facilitate flow of fluid and this will be described in greater detail below. Referring to FIG. 14, there is illustrated in section view the base 90 and the collar 91. Collar 91 contains an internal opening (illustrated in FIG. 15) through which part of the plunger 84 can pass. This is illustrated in FIGS. 14, 16, 18, 19 and 21.

In use, the valve assembly is initially in the position illustrated in FIG. 14 where plunger 84 is in the fully retracted position such that the end face 87 is substantially flush with inlet 82.

When a medical device (e.g. a tip 93) is pushed into inlet 82 (this being illustrated in FIG. 16), this will cause the plunger 84 to be pushed forwardly and will cause the resilient web 85 to stretch and will enlarge the variable volume chamber, this having been described previously. Base 90 is fixed to housing part 80 of the valve assembly and therefore does not move upon movement of the plunger 84. Similarly, collar 91 is attached to base 90 and does not slide with the plunger.

Figure 16:
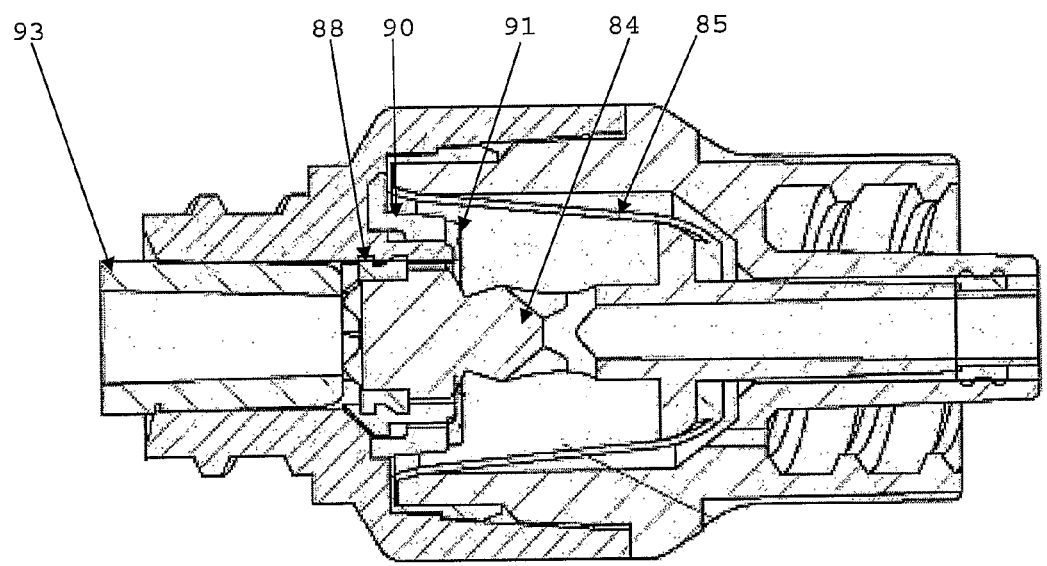

When the medical tip 93 has been pushed into inlet 82 as illustrated in FIG. 16, the annular seal 88 extending about plunger 84 has now moved to an enlarged portion when fluid can now flow through tip 93 and past seal 88.

Figure 17:
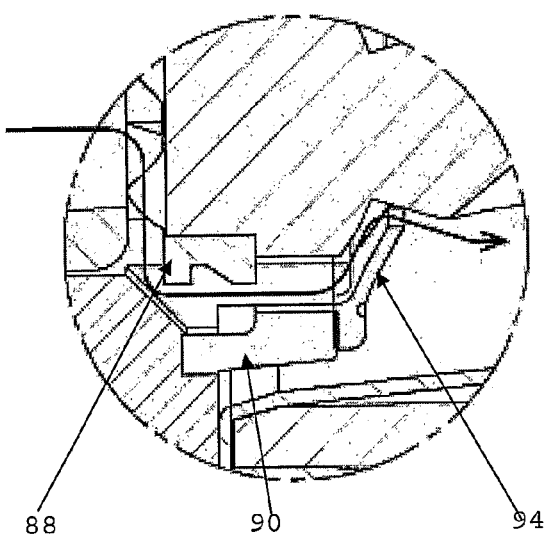
Figure 18:
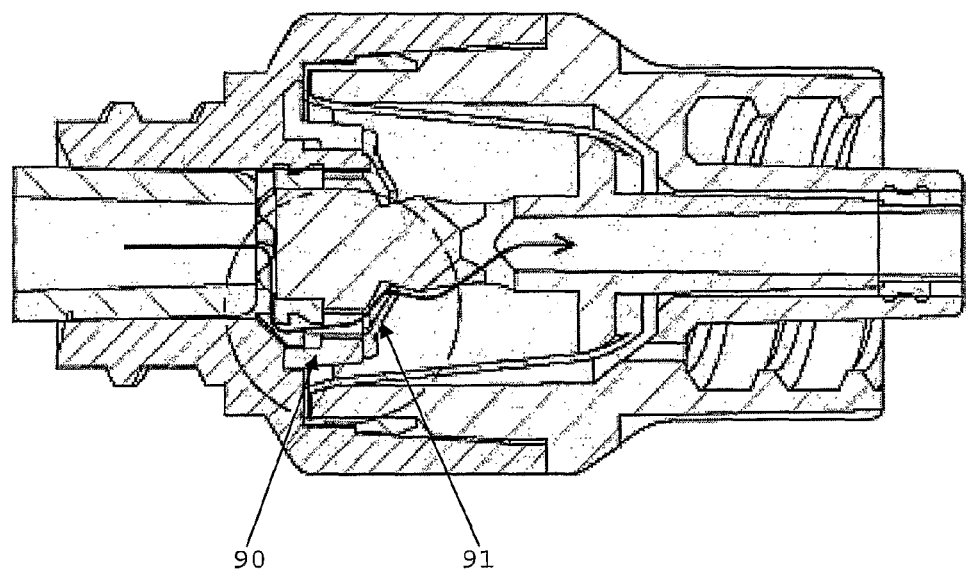

When fluid is caused to flow through the medical tip 93, the force of the fluid will push the resilient flaps 94 (see FIG. 15) of collar 91 into an open position therefore allowing fluid to flow through the valve assembly. FIG. 17 illustrates this particular position where flaps 94 have been pushed under the force of the fluid flow to no longer engage with plunger 84. Instead, a fluid flow pathway is formed.

Figure 19:
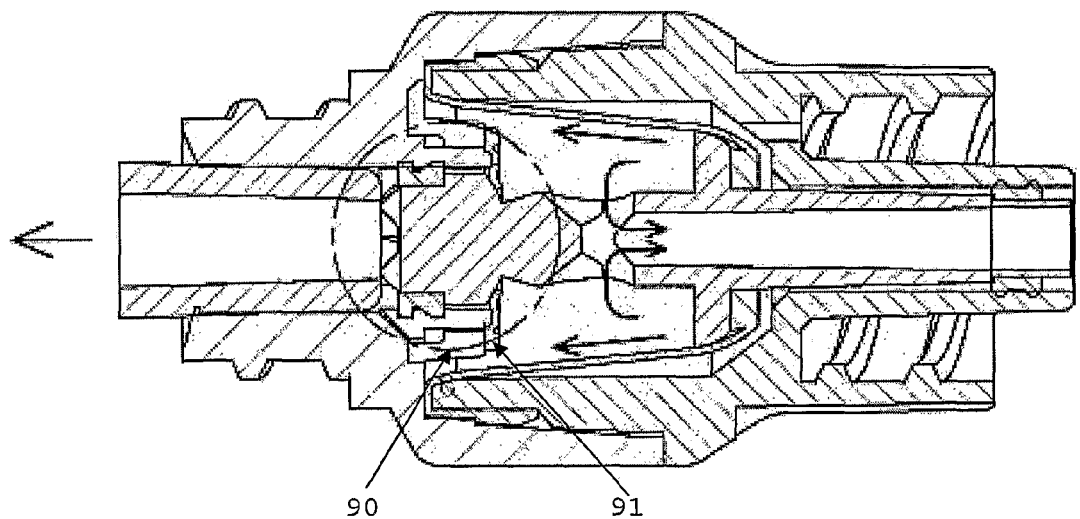

As soon as the fluid flow is stopped, the flaps 94 spring back to the sealing position where they seal against plunger 84 such that backflow is reduced or is eliminated. This position is illustrated in FIG. 19. However there is still the possibility of some blood flowing into the end face area 87 of the plunger such that when the plunger moves back to the retracted position illustrated in FIG. 14, there will be blood around the inlet 82 of the valve assembly.

Figure 20:
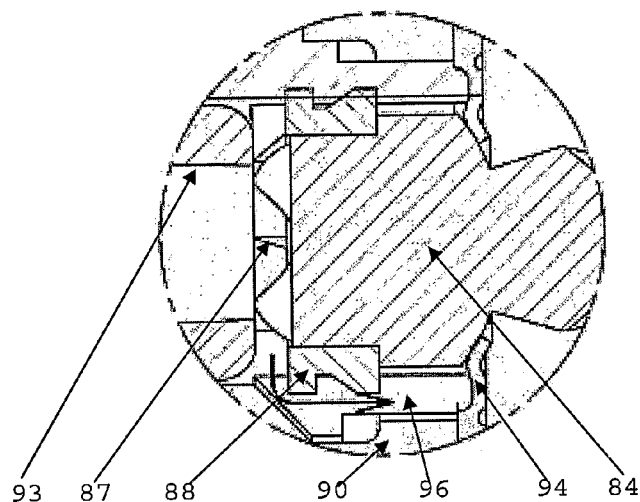

This can be reduced or eliminated by the embodiment illustrated in FIGS. 16-21. Referring particularly to FIG. 20, this is the position immediately after fluid flow has stopped and the tip 93 is beginning to be withdrawn. At this stage, the flaps 94 are sealed against the plunger 84. The annular seal 88 on the plunger body has not yet moved into sealing engagement with the passageway in the housing and therefore fluid can still flow from the end face area 87 and into a temporary chamber 96 (see FIG. 20). Upon retraction of the tip (by a few millimeters), the plunger body 84 will begin movement back to the retracted position (also by a few millimeters), and this will cause the size of volume of the temporary chamber 96 to increase. In turn, this causes the pressure in the temporary chamber to drop and this pressure drop will cause any blood still in the end face area 87 to be "sucked" into the temporary chamber.

Figure 21:
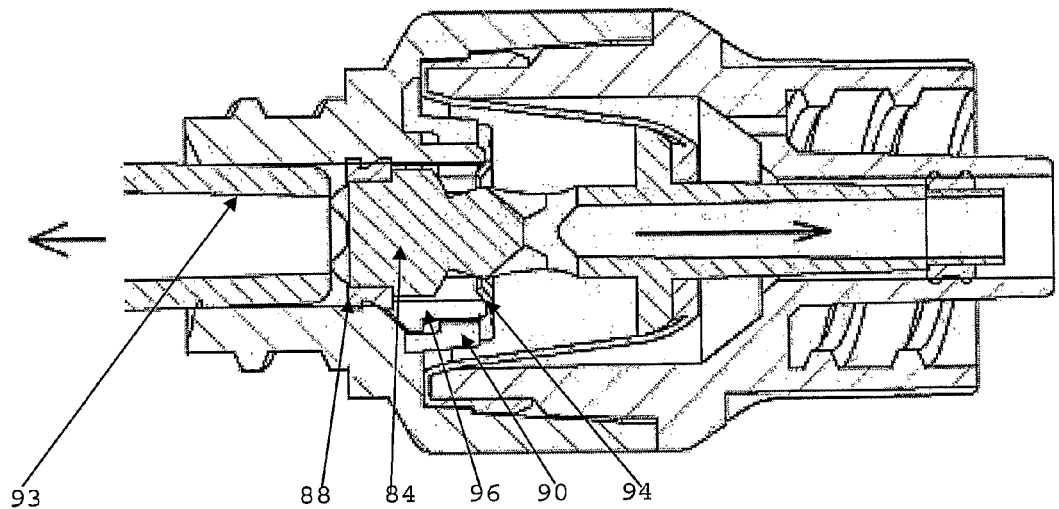

Further retraction of tip 93 (typically by a few more millimeters) will now cause the plunger to be retracted sufficiently such that the annular seal 88 is now sealingly engaged with the internal passageway of this part of the valve assembly, this position being illustrated in FIG. 21. In this position, the temporary chamber 96 is now sealed (by annular seal 88) which means that blood can not flow back to the end face area 87 upon further retraction of the tip 93 and therefore further retraction of plunger 84.

Figure 22:
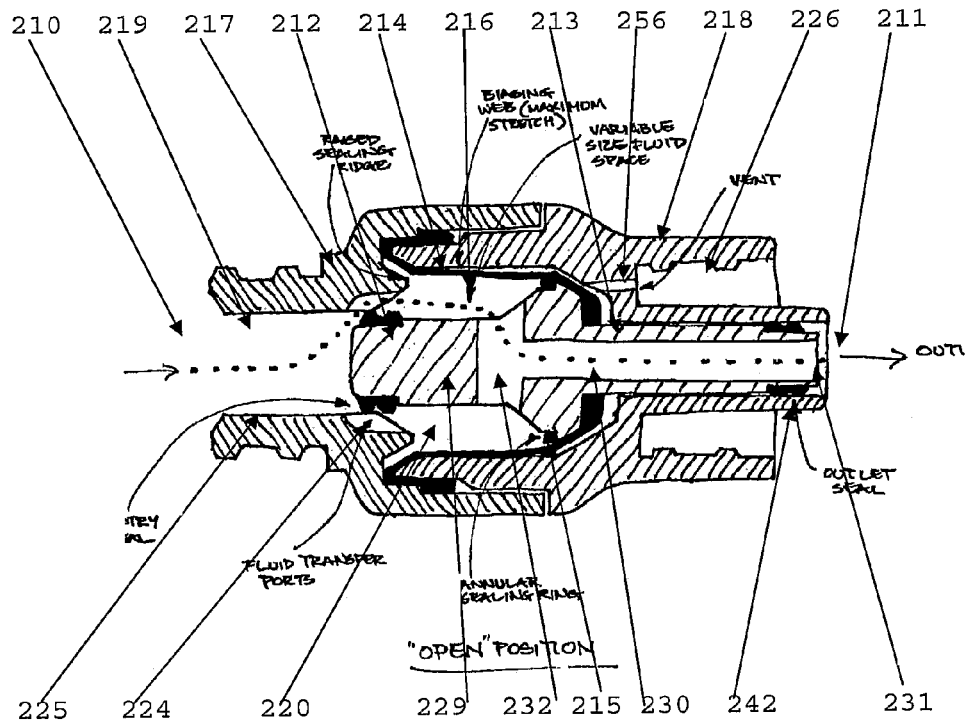
FIGS. 22-24. Illustrate a sixth embodiment of the invention.
Figure 23:
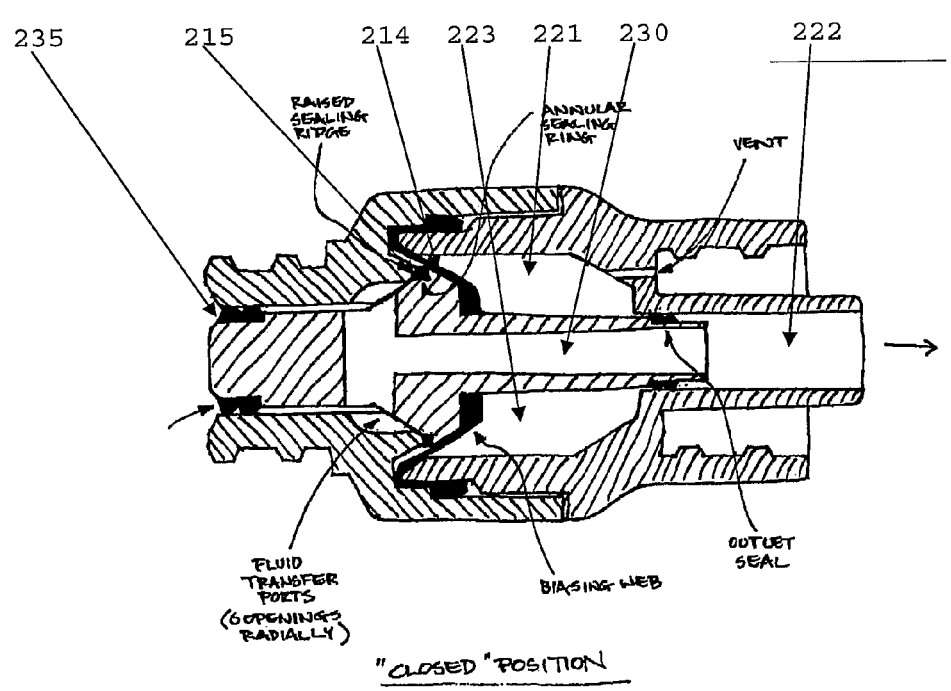
Figure 24:
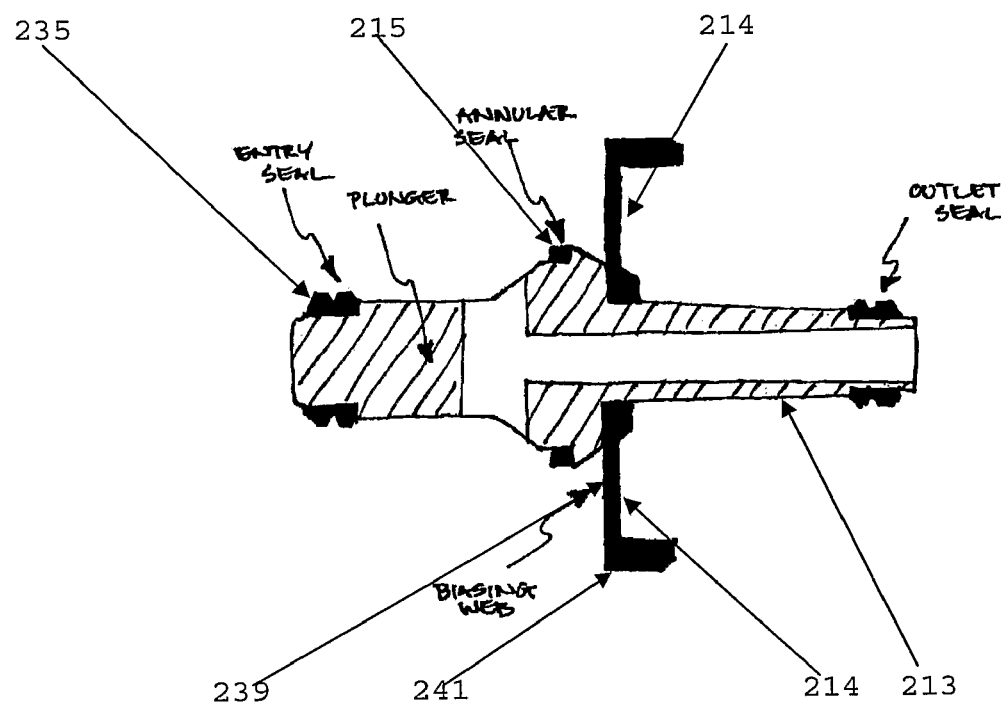

Referring to FIGS. 22-24 and initially to FIG. 22, there is illustrated a valve assembly which comprises an inlet 210 and an outlet 211, a flow pathway that extends through the valve assembly from inlet 210 to outlet 211, a plunger 212 that is positioned in the flow pathway and which can reciprocate between a forward open position illustrated in FIG. 22, and a retracted closed position illustrated in FIG. 23, the plunger having an elongate forward nose portion 213, an elastic web 214 which extends about plunger 212, and a variable volume chamber 216 which is larger in FIG. 22 and smaller or nil in FIG. 23.

Referring to the parts in greater detail, the valve assembly in the embodiment comprises an outer body that is formed of two parts that are attached together, the two parts being a first part 217 and a second part 218. These parts are formed of plastic material and are joined together by any suitable method. Part 217 is substantially hollow. Part 217 comprises an outer passageway 219 which is circular and which has a smaller diameter, and an inner passageway 220 which is also circular and which has a substantially larger diameter. Similarly, part 218 has an inner passageway 221 that has a substantially larger diameter than outer passageway 222. When the two parts are joined, the two larger diameter passageways together form an internal chamber 223. Outer passageway 222 terminates in outlet 211, while outer passageway 219 terminates in inlet 210.

The outer passageway 219 in part 217 contains six radial open ended fluid transfer ports 224. Ports 224 comprise recesses in the wall of outer passageway 219 and are open ended which means that the ports communicate with chamber 216. The ports 224 do not extend entirely along the wall of passageway 219. Rather, the ports terminate partway along the wall such that a smooth wall portion 225 extends between the end of ports 224 and inlet 210. The reason for this will be described in greater detail below.

Part 218 contains a standard luer lock fitting 226 which extends about passageway 222 and which functions to allow a needle etc to be attached to this part of the assembly. Of course, other types of attachments can also be used.

Inner passageway 221 has a diameter that is smaller than inner passageway 220. Thus, the wall 227 of inner passageway 221 passes into inner passageway 220 this being best illustrated in FIG. 23. Moreover, wall 227 has a length that results in the wall 227 being spaced somewhat from wall 228 of top part 217 (see FIG. 23). This spacing facilitates the attachment of the elastic web that will be described in greater detail below.

Plunger 212 is formed of plastic material and comprises a unitary body. The plunger has a particular configuration that provides a nose portion 213, and a rear body portion 229. Nose portion 213 is slightly tapered and has a through passageway 230 which passes through an open outer end 231 and functions to allow fluid to flow through the valve assembly. Body portion 229 is provided with a transverse through bore 232 through which fluid can pass. Body portion 229 has a substantially cylindrical outer wall provided with an entry seal 235. This is why the fluid ports 224 in end wall 225 terminate short of inlet 210 to also provide a smooth area which functions as a sealing zone 236. Thus, when the plunger is in the closed position illustrated in FIG. 23, the sealing collar 235 seals against the sealing zone 236 to provide seal against fluid flow.

When plunger 212 is pushed forwardly from the position illustrated in FIG. 23 to the position illustrated in FIG. 22, the plunger only moves by a few mm, but this movement is sufficient to move seal 235 away from sealing zone 236 and into the area of the flow ports 224 and to allow fluid to pass along the outside wall of body portion 229, through the fluid ports 224, through bore 232 through passageway 230 and through outlet 211. Conversely, when the plunger is retracted from the position illustrated in FIG. 22 to the position illustrated in FIG. 23 the plunger again seals against passage of fluid from inlet 210 through outlet 211.

Fluid only flows when the flow ports 224 are opened by seal 235 moving past the outer most edge of the flow ports. At all other times a seal is maintained between the internal wall 225 and collar 235.

The plunger is biased back to its retracted position by the elastic web 214 which also provide additional functions. Elastic web 214 is made of a rubbery elastic material having an excellent memory. The elastic web is substantially circular and has a base portion 239 with a peripheral edge 241 that is thickened with respect to the thickness of the base portion immediately next to the peripheral edge. The thickened peripheral edge 241 is trapped between wall 227 of part 218 and the inner wall of part 217. Peripheral edge 241 also functions to seal the fluid pathway in the apparatus.

The plunger 212 has an annular seal 215 on body portion 229. The annular seal 215 is positioned on body portion 229 such that when the plunger is in the retracted or closed position illustrated in FIG. 23, the annular seal sits between body portion 229 and an internal wall of the valve. The annular seal provides two functions. The first function is to stop direct contact between the plunger and the internal wall of the valve and thereby to reduce wear and tear. The second function is to close off the variable volume chamber 216 when the variable volume chamber is in the smaller position. Thus, when the plunger is in the closed position, the variable volume chamber is isolated from the remainder of the fluid pathway in the valve and there is no possibility of any fluid passing into the variable volume chamber or flowing from the variable volume chamber when the plunger is in the retracted closed position.

The nose portion of the plunger is provided with an outlet seal 242.

As the plunger 212 is pushed to the forward open position, it will stretch the biasing web 214 which forms part of the variable volume chamber 16 and the movement will increase the volume of chamber 216. When the plunger is retracted to the closed position (and web 214 forms part of a biasing means to bias the plunger back to the closed position), the variable volume chamber will reduce in volume and will provide a positive pressure in the valve to prevent backflow of any fluid into outlet 211. This arrangement is similar to that described in our earlier international patent application.

The web is designed such that when the plunger 212 is in the retracted closed position, there is still some tension in the web to keep the plunger in the retracted position.

A small air passageway 256 is provided to allow air to pass into chamber 223 upon shrinking of the web and to allow air to pass out of chamber 223 upon stretching of the web.

The valve assembly prevents back flow of fluids by maintaining a positive pressure in chamber 216.

Another advantage with the arrangement is that possibly contaminated air is kept separate from the fluid flow pathway of the valve assembly by virtue of the web 214 and the various seals.

It should be appreciated that various other changes and modifications can be made to the invention without departing from the spirit and scope of the invention.

What is claimed is:

1. A one way valve assembly that comprises:
   an inlet and an outlet,
   a flow pathway that extends through the valve assembly from the inlet to the outlet,
   a plunger that is positioned in the flow pathway and which can move between a forward open position where fluid can flow from the inlet to the outlet, and a retracted closed position where fluid flow is reduced or prevented from flowing from the inlet to the outlet,
   an at least partially elastic diaphragm that has an outer end fixed to the valve assembly, and an inner portion which engages with the plunger such that reciprocation of the plunger from the retracted position to the forward position causes at least part of the diaphragm to stretch,
   a variable volume chamber having walls at least partially defined by the plunger and the diaphragm, the chamber forming part of the flow pathway, the chamber having smaller or nil volume when the plunger is in the retracted position, and a larger volume when the plunger is in the extended position, whereby upon retraction of the plunger, the variable volume chamber reduces in volume which results in a pumping action to pump fluid through the fluid pathway towards the outlet, thereby reducing or preventing backflow, and
   a resilient end valve positioned within the flow pathway adjacent the inlet and supported by a spacing member, the spacing member being co-axially aligned with the flow pathway and attached to the plunger, the resilient end valve being movable between an open flexed position enabling fluid to flow towards the outlet of the valve, and a closed rest position preventing backflow of fluid through the inlet, wherein the resilient end valve is moved to the open flexed position by the flow of fluid, and the resilient end valve is moved to the closed rest position by the absence of flow of fluid.

2. The assembly as claimed in claim 1, wherein the resilient end valve is naturally biased to the closed rest position and is moved to the open flexed position by the flow of fluid through the inlet and will move to the naturally closed rest position when the flow of fluid stops.

3. The assembly as claimed in claim 2 wherein the plunger is a sliding plunger that is moved from the retracted position to the forward position upon insertion of a tip into the inlet of the valve assembly, and moves from the forward position to the retracted position upon removal of the tip from the inlet.

4. The assembly as claimed in claim 3, wherein the resilient end valve moves with the plunger such that when the plunger moves between the forward position and the retracted position.

5. The assembly as claimed in claim 4, wherein the plunger has a base part that is adjacent the inlet of the valve assembly, the spacing member towards the inlet from the base part, and has a smaller cross-section size than resilient end valve to support a central portion of the resilient end valve, the resilient end valve comprises a disk-like member having a peripheral edge that can flex relative to the central portion, the peripheral edge able to flex between a closed rest position where the peripheral edge prevents fluid from backflowing through the valve assembly, and a flexed open position where fluid can flow through the valve assembly, the resilient end valve flexing to the open position by the pressure of fluid flowing through the inlet, and returning to the closed rest position upon reduction of the fluid pressure through the inlet.

6. A one-way valve assembly that comprises an inlet and an outlet, a variable volume chamber which increases in volume as fluid flows through the assembly from the inlet to the outlet, and which decreases in volume upon removal of a tip from the inlet, or upon slowing or stopping of fluid flow from the inlet to the outlet, the decrease in volume providing a positive pressure to reduce or to prevent backflow, and a resilient end valve positioned within the flow pathway adjacent the inlet and at least partially supported by a spacing member that is co-axially aligned with the flow pathway and attached to a plunger, the resilient end valve being movable between an open flexed position where fluid can flow from the inlet to the outlet, and a closed rest position where backflow is reduced or prevented, the resilient end valve being movable from the closed rest position to the open flexed position by fluid pressure, and being movable from the open flexed position to the closed rest position upon a reduction or stopping of the fluid pressure.

7. A medical fluid dispensing device having:
   a body adapted to contain fluid, a tip defined by the body with a forward opening through which fluid is dispensed, and a mechanism for dispensing fluid via the tip; and
   a one-way valve assembly that comprises:

an inlet and an outlet, wherein the tip of the medical fluid dispensing device is inserted into the inlet of the valve assembly, a flow pathway that extends through the valve assembly from the inlet to the outlet, a plunger that is positioned in the flow pathway and which can move between a forward open position where fluid can flow from the inlet to the outlet, and a retracted closed position where fluid flow is reduced or prevented from flowing from the inlet to the outlet, an at least partially elastic diaphragm that has an outer end fixed to the valve assembly, and an inner portion which engages with the plunger such that reciprocation of the plunger from the retracted position to the forward position causes at least part of the diaphragm to stretch, a variable volume chamber having walls at least partially defined by the plunger and the diaphragm, the chamber forming part of the flow pathway, the chamber having smaller or nil volume when the plunger is in the retracted position, and a larger volume when the plunger is in the extended position, whereby upon retraction of the plunger, the variable volume chamber reduces in volume which results in a pumping action to pump fluid through the fluid pathway towards the outlet, thereby reducing or preventing backflow, and a resilient end valve positioned within the flow pathway adjacent the tip and a supporting spacing member such that the resilient end valve is positioned between the tip and the spacing member, the spacing member being co-axially aligned with the flow pathway and attached to the plunger, the resilient end valve being movable between an open flexed position enabling fluid to flow towards the outlet of the valve, and a closed rest position preventing backflow of fluid through the inlet, wherein the resilient end valve is moved to the open flexed position by the flow of fluid, and the resilient end valve is moved to the closed rest position by the absence of flow of fluid.

* * * * *